United States Patent [19]

Prugh et al.

[11] Patent Number: 4,798,831

[45] Date of Patent: Jan. 17, 1989

[54] SUBSTITUTED THIENO[2,3-B]FURAN-2-SULFONAMIDES AS ANTIGLAUCOMA AGENTS

[75] Inventors: John D. Prugh, Chalfont; George D. Hartman, Lansdale; Wasyl Halczenko, Hatfield, all of Pa.

[73] Assignee: Merck & Co., Inc., Rahway, N.J.

[21] Appl. No.: 190,183

[22] Filed: May 4, 1988

Related U.S. Application Data

[63] Continuation-in-part of Ser. No. 162,545, Mar. 1, 1988, abandoned, which is a continuation-in-part of Ser. No. 97,003, Sep. 16, 1987, abandoned.

[51] Int. Cl.$^4$ .................... A61K 31/38; C07D 495/02; C07D 403/00; C07D 421/00
[52] U.S. Cl. .................................................. 514/253; 514/275; 514/333; 514/338; 514/397; 514/443; 514/228.2; 544/146; 544/295; 514/233.8; 544/296; 544/297; 544/357; 544/405; 546/270; 548/336; 549/50

[58] Field of Search ............... 514/231, 253, 275, 333, 514/338, 397, 443; 544/146, 295, 296, 297, 357, 405; 546/270; 548/336; 549/50

[56] References Cited

U.S. PATENT DOCUMENTS 3,733,322  5/1973  Wright ................................. 549/50
4,668,697  5/1987  Shepard et al. ..................... 514/443

FOREIGN PATENT DOCUMENTS 2378783  9/1978  France .............................. 514/443

OTHER PUBLICATIONS

Kvitko et al., J. Org. Chem. (USSR) 12, 1550 (1976).

Primary Examiner—Alan Siegel
Attorney, Agent, or Firm—William H. Nicholson; Michael C. Sudol, Jr.

[57] ABSTRACT

Thieno[2,3-b]furan-2-sulfonamides are carbonic anhydrase inhibitors useful in the treatment of elevated intraocular pressure and glaucoma.

14 Claims, No Drawings

SUBSTITUTED THIENO[2,3-B]FURAN-2-SULFONAMIDES AS ANTIGLAUCOMA AGENTS

SUMMARY OF THE INVENTION

This is a continuation-in-part of application Ser. No. 162545 filed Mar. 1, 1988 now abandoned which in turn is a continuation-in-part of application Ser. No. 097003 filed Sept. 16, 1987 now abandoned.

This invention relates to novel aromatic sulfonamides useful in the treatment of elevated intraocular pressure. More particularly this invention relates to compounds having the structural formula:

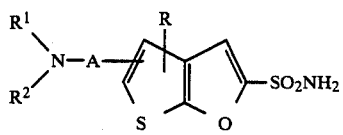

wherein A, R, $R^1$, and $R^2$ are as hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma. The invention also relates to processes for preparation of the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

DETAILED DESCRIPTION OF THE INVENTION

The novel compounds of this invention have structural formula:

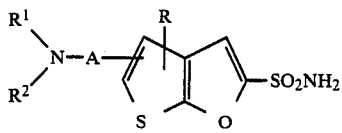

or a pharmaceutically acceptable salt thereof, wherein
A is $C_{1-8}$ alkylene, either straight or branched chain and either unsubstituted or substituted with $C_{1-3}$ alkoxy or hydroxy; and
R is hydrogen or $C_{1-6}$ alkyl, either straight or branched chain; and
$R^1$ and $R^2$ are independently:
(1) hydrogen,
(2) $C_{1-6}$ alkyl, either unsubstituted or substituted with one or more of
  (a) $C_{1-3}$ alkoxy,
  (b) $C_{1-3}$alkoxy-$C_{2-4}$alkoxy,
  (c) hydroxy,
  (d) phenyl,
  (e) halo such as chloro, bromo or fluoro,
  (f) heteroaromatic such as pyridyl, pyrimidinyl, pyrazinyl or imidazolyl, or
  (g) —$NR^3R^4$ wherein $R^3$ and $R^4$ are independently selected from
    (i) hydrogen and
    (ii) $C_{1-6}$ alkyl, either unsubstituted or substituted with one or more of $C_{1-3}$ alkoxy, hydroxy or phenyl, or

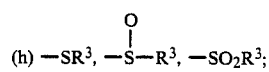

or
(3) taken together with the nitrogen atom to which they are attached form a 5 to 7-membered heterocycle such as piperidine, morpholine, thiomorpholine, thiomorpholine-S-oxide, thiomorpholine-S,S-dioxide, piperazine, or N-$C_{1-3}$ alkylpiperazine.

A preferred embodiment of the novel compounds is that wherein A is joined to the 5-position of the thieno[2,3-b]furan ring system.

It is still more preferred that A is $-(CH_2)-_{1-3}$, especially $-CH_2$.

The novel processes for preparing the novel compounds of this invention are illustrated as follows, wherein Ar represents

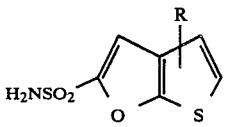

and A' represents $C_{0-7}$alkylene either unsubstituted or substituted with $C_{1-3}$alkoxy or hydroxy:

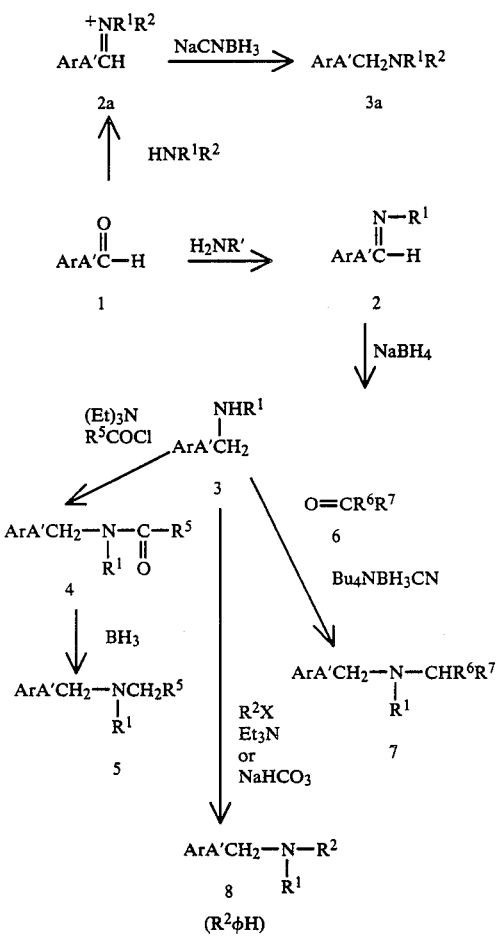

The process comprises treating the aldehyde, 1, in the presence of a slight excess of HCl gas with the amine $H_2NR^1$ or $HNR^1R^2$ at about 15° to 60° C. in a $C_{1-3}$ lower alkanol solvent such as methanol or ethanol for about 0.5 to 4 hours. The crystalline precipitate of 2 or 2a is redissolved by addition of THF or isolated and dissolved in methanol and THF and treated with a complex metal hydride such as sodium borohydride in the case of 2 or sodium cyanoborohydride in the case of 2a at about 0° to 20° C. and continuing stirring for about 0.5 to 6 hours.

Compound 3 is converted into a tertiary amine either by acylation to 4 and reduction to 5, or by treatment with ketone 6, followed by reduction to give 7. Conversion of 3 to 4 would be carried out in an aprotic solvent such as ether, THF, or the like in the presence of a base such as triethylamine at about room temperature and the subsequent reduction to 5 by $BH_3.S(CH_3)_2$ would be carried out at about room temperature in a solvent such as toluene, $CH_2Cl_2$ or THF.

Conversion of 3 to 7 would be carried out by treatment of 3 with an equivalent amount of ketone 6 at about room temperature in a solvent such as a halocarbon (methylene chloride) or an alcohol, such as methanol.

Alternatively, secondary amine 3 can be converted into tertiary amine 8 simply by alkylation. Thus, treatment of 3 in ether, THF, DMF or halocarbon solution with an alkyl halide, $R^2X$, (iodide bromide or chloride) in the presence of an organic $((C_2H_5)_3N)$ or inorganic ($NaHCO_3$) base would give 8.

Those novel compounds wherein A is branched chain alkylene can be prepared either from the aldehyde as shown in the above reaction schemes wherein A' is a branched chain alkylene, or from the aromatic aldehyde as shown below:

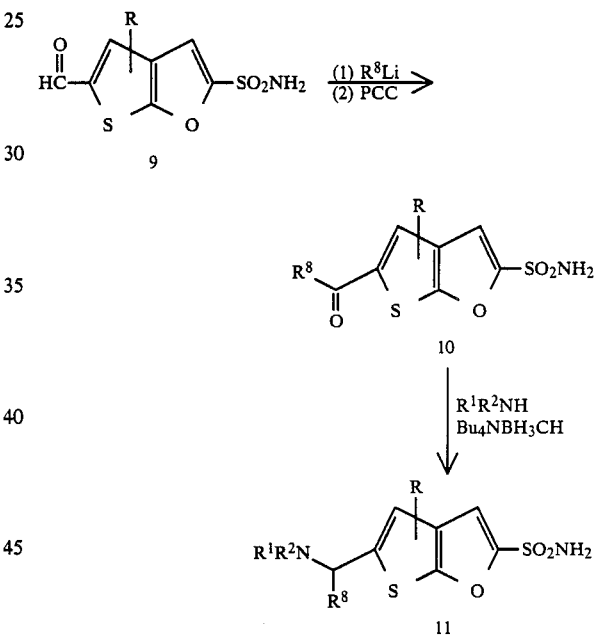

In this process 9 is treated with organolithium reagent $R^8Li$ in ether or THF at −78° to −30° C., this is quenched with $H_2O$ and the product extracted. This alcohol is oxidized to ketone 10 with pyridinium chlorochromate (PCC) in $CH_2Cl_2$ at room temperature (2–3 hours). The ketone 10 is reductively aminated with amine $R^1R^2NH/Bu_4NBH_3CH$ in an alcohol ($CH_3OH$) at room temperature for 1–5 hours to provide 11. In this manner the following compounds are made:

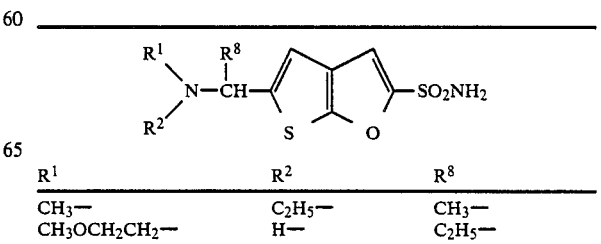

| $R^1$ | $R^2$ | $R^8$ |
| --- | --- | --- |
| $CH_3-$ | $C_2H_5-$ | $CH_3-$ |
| $CH_3OCH_2CH_2-$ | $H-$ | $C_2H_5-$ |

-continued

R¹\N(R²)-CH(R⁸)- [connected to thieno-furan ring] -SO₂NH₂

| R¹ | R² | R⁸ |
|---|---|---|
| C₆H₅CH₂— | HOCH₂CH₂— | (CH₃)₂CH— |
| CH₃OCH₂CH₂— | CH₃OCH₂CH₂— | CH₃— |
| CH₃OCH₂CH₂— | HOCH₂CH₂— | CH₃OCH₂CH₂— |
| FCH₂CH₂— | CH₃OCH₂CH₂— | CH₃CH₂— |
| —(CH₂)₂—O—(CH₂)₂— | | CH₃OCH₂CH₂— |
| —(CH₂)₂—S—(CH₂)₂— | | CH₃— |

The novel pharmaceutical formulations of this invention are adapted for topical ocular administration in the form of solutions, ointments, solid water soluble polymeric inserts, or solutions which gel at body temperature or in the presence of lachrymal fluids for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of an effective amount of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

5-(Isobutylaminomethyl)thieno[2,3-b]furan-2-sulfonamide hydrochloride

Step A: Preparation of 2-(Carbomethoxymethylthio)-3-[2-(1,3-dioxolanyl)]furan

To a mechanically stirred solution of 69.0 g (0.49 mol) of 3-[2-(1,3-dioxolanyl)]furan in 250 ml of THF under N₂ and cooled to −78° C. was added 0.49 mol of n-butyllithium (in hexane) dropwise at <−70° C. This was stirred at −78° C. for 40 minutes to provide a white suspension. Sulfur (16.64 g, 0.52 mol) was added via Gooch tubing portionwise as the temperature rose to −65° C. to provide an orange suspension which was stirred at −78° C. for 0.5 hours and then at −50° C. for 0.5 hour to afford a deep purple reaction mixture. Methyl bromoacetate 91.8 g (0.60 mol) in 50 ml THF was added dropwise at −78° C. to give a brownish suspension that was stirred at −70° C. for 0.5 hour and then was allowed to gradually warm to 0° C. over 1.5 hours.

The reaction mixture was quenched with a mixture of 250 ml brine/250 ml ether. The aqueous phase was separated, re-extracted with 200 ml of ether and the organic phases were combined, washed with brine, dried and evaporated to dryness in vacuo. The resulting oil was taken up in ether and passed through a silica gel pad to provide a clear filtrate. The solvent was removed in vacuo to give the title compound as an oil: $R_f$ 0.4 on silica gel eluting with 20% ethyl acetate/hexanes.

Step B: Preparation of 2-(Carbomethoxymethylthio)furan-3-carboxaldehyde

To a solution of 6.8 g (0.028 mol) of product from Step A dissolved in 50 ml acetone was added 100 mg p-toluenesulfonic acid monohydrate and the resulting solution was kept at room temperature for 3.0 hours. Saturated NaHCO₃ solution (15 ml) was added and the resulting suspension was stripped in vacuo. The residue was extracted with 2×40 ml portions of ether and the combined organic extracts were washed with brine and dried. The solvent was removed in vacuo to give the title compound as a clear oil: $R_f$ 0.5 on silica gel eluting with 20% ethyl acetate/hexanes.

Step C: Preparation of Methyl Thieno[2,3-b]furan-5-carboxylate

To a solution of 89.0 g (0.58 mol) 1,8-diazabicyclo[5.4.0]undec-7-ene in 1.5 l of THF at room temperature was added 78.5 g (0.39 mol) of product from Step B in 500 ml THF dropwise and the resulting solution was stirred for 24 hours. The THF solution was decanted from the black, tarry residue and the solvent was evaporated in vacuo. The residue was taken up in ether, washed with water, brine and dried. The solvent was removed in vacuo to give a residue that was triturated with 50 ml of 50% 2-propanol/hexane to give a pale yellowish solid. The filtrate was evaporated and the residue was purified by flash chromatography on silica gel eluting with 8% ethyl acetate/hexane to afford pure title compound, $R_f$ 0.4. This was combined with the solid isolated initially after trituration with hexane, to give title compound as a white solid, m.p. 86°–88° C.

Step D: Preparation of Thieno[2,3-b]furan-5-carbinol

To a suspension of 3.80 g (0.1 mol) of lithium aluminum hydride in 500 ml ether cooled to 0°–10° C. was added a solution of 9.1 g (0.05 mol) of product from Step C in 150 ml ether dropwise over 20 minutes. This suspension was stirred at room temperature for 4 hours and was then cooled and quenched by dropwise addition of 30 ml of saturated Na+/K+ tartrate solution. This suspension was stirred at room temperature for 0.5 hour and the ether phase was decanted from the gummy solid. This solid was triturated with ether and the combined organic phases were washed with brine and dried. The solvent was removed in vacuo to provide the title compound as an oil: $R_f$ 0.3 on silica gel eluting with 20% ethyl acetate/hexane.

Step E: Preparation of Thieno[2,3-b]furan-5-carboxaldehyde

To a stirred suspension of 1.43 g (6.6 mmol) of pyridinium chlorochromate in 15 ml methylene chloride at room temperature was added 0.68 g (4.4 mmol) of product from Step D in 15 ml methylene chloride in one portion and the resulting dark suspension was stirred at room temperature for 2 hours. The reaction mixture was diluted with 20 ml CH₂Cl₂ and was filtered through a silica gel pad. The solvent was removed in vacuo to give the title compound as a viscous yellow oil: $R_f$ 0.4 on silica gel eluting with 20% ethyl acetate/hexane.

Step F: Preparation of 5-[2-(1,3-Dioxolanyl)]thieno[2,3-b]furan

To a solution of 5.91 g (0.029 mol) of product from Step E and 4.96 g (0.08 mol) ethylene glycol in 75 ml benzene was added 100 mg pyridinium p-toluenesulfonate and the resulting solution was heated at reflux utilizing a Dean-Stark trap. After 5 hours all starting material was consumed. The cooled reaction mixture was diluted with 75 ml water and the organic phase was separated and dried. This was filtered through a pad of silica gel and the solvent was removed in vacuo to give the title compound as an oil: $R_f$ 0.6 on silica gel eluting with 20% ethyl acetate/hexane.

Step G: Preparation of 5-[2-(1,3-Dioxolanyl)]thieno[2,3-b]furan-2-sulfonamide To a solution of 1.96 g (0.01 mol) of product from Step F in 20 ml THF cooled to −78° C. under $N_2$ was added 0.01 mol n-butyllithium dropwise at <−70° C. and the resulting solution was stirred for 45 minutes at −78° C. Sulfur dioxide gas was introduced close to the surface of the reaction mixture as the temperature rose to about −60° C. The suspension was stirred at −65° C. for 0.5 hours while $SO_2$ gas was continuously admitted and then allowed to gradually warm to 0° C. over 1.0 hour. The solvent was removed at <35° C. at water aspiration pressure to afford a tan solid. This solid was taken up in 20 ml of saturated $NaHCO_3$ solution and with cooling to 0°-10° C., 2.0 g (0.015 mol) of N-chlorosuccinimide was added portionwise over 5 minutes. The resulting suspension was stirred vigorously at 0°-10° C. for 1.5 hours. This was extracted with 3×50 ml portions of $CHCl_3$ and the combined organic extracts were washed with brine and dried. The solvent was removed in vacuo to give the intermediate sulfonyl chloride as a tan solid. This was dissolved in 15 ml acetone and with cooling to 0°-10° C., 15 ml $NH_4OH$ solution was added in one portion. This was stirred at 0°-10° C. for 1.5 hours and then extracted with 5×50 ml portions of ethyl acetate. The combined organic extracts were washed with brine, dried and the solvent removed in vacuo to give the title compound as a tan solid.

Step H: Preparation of 5-Formylthieno[2,3-b]furan-2-sulfonamide

To a solution of 1.66 g (0.006 mol) of product from Step G in 35 ml acetone was added about 100 mg p-toluenesulfonic acid monohydrate and the resulting solution was kept at room temperature for 2 hours. This was treated with 25 ml of a saturated $NaHCO_3$ solution and the organic solvent was removed in vacuo. The residue was extracted with 5×50 ml portions of ethyl acetate and the combined organic layers were washed with brine and dried. The solvent was removed in vacuo to give the title compound as a tan solid: $R_f$ 0.5 on silica gel eluting with 50% ethyl acetate/hexane, m.p. 165°-167° C.

Step I: Preparation of 5-(Isobutylaminomethyl)thieno[2,3-b]furan-2-sulfonamide hydrochloride To a suspension of 0.465 g (2.0 mmols) of product from Step H in 5 ml ethanol at room temperature was added 1.02 g (14.0 mmols) of isobutylamine and the resulting solution was stirred at room temperature for 1.0 hour. Then, 0.30 g (8.0 mmols) of sodium borohydride was added at room temperature and this suspension was stirred for 2 hours. The reaction mixture was then poured into 75 ml water and was acidified with 6N HCl. This acidic mixture was neutralized with aqueous ammonium hydroxide to pH 8-9 and extracted with 4×50 ml portions of ethyl acetate. The organic extracts were combined, washed with brine and dried. The solvent was removed in vacuo to give the free base of the title compound as a pale yellow residue. This was purified by flash chromatography on silica gel eluting with 5% methanol/chloroform to provide pure free base as a white solid: $R_f$ 0.3 on silica gel eluting with 5% methanol/chloroform. This was dissolved in 10 ml ethanol, treated with ethanolic HCl and the resulting solution was gradually diluted with 30 ml ether while being cooled in an ice bath to provide the title compound as a white solid, m.p. 237°-242° C.

Employing the procedures substantially as described in Example 1, Step I but substituting for the isobutylamine used therein approximately equimolar portions of the amines of structure $R^1R^2NH$ depicted in Table I there are produced the $R^1R^2$-aminomethylthieno[2,3-b]furan-2-sulfonamides, also depicted in Table I:

TABLE I $$\text{HC(=O)-[thieno[2,3-b]furan]-SO}_2\text{NH}_2 \xrightarrow{\text{(1) } R^1R^2NH,\ \text{(2) NaBH}_4,\ \text{(3) H}^\oplus} R^1R^2N-CH_2-[\text{thieno[2,3-b]furan}]-SO_2NH_2$$

| $R^2$ | $R^1$ | melting or decomp point (°C.) |
|---|---|---|
| H | $CH_3-$ | 220-223 (HCl) |
| H | $C_2H_5-$ | 225-229 (dec) (HCl) |
| H | pyridyl-$CH_2-$ | 149-151 (maleate) |
| H | $HO(CH_2)_4-$ | 218-220 (HCl) |
| H | $CH_3OCH_2CH_2-$ | 190-192° (HCl) |
| H | $CH_3OCH_2CH_2CH_2-$ | 203-205° (HCl) |
| H | $C_2H_5O(CH_2)_2-$ | 200.5-202.5 HCl |
| H | $CH_3O(CH_2)_2O(CH_2)_3-$ | 182-184 (HCl) |
| H | $n\text{-}C_3H_7-$ | 251-254 (HCl) |
| $-CH_2CH_2-O-CH_2CH_2-$* | | 243-246 (HCl) |
| $CH_3OCH_2CH_2-$ | $CH_3OCH_2CH_2-$* | 95-97 (maleate) |
| H— | $FCH_2CH_2-$ | 202-204 (HCl) |

*Intermediate iminium compound was reduced with sodium cyanoborohydride rather than sodium borohydride.

Employing the procedures described in the foregoing the compounds depicted in the following Table also are prepared from the appropriate starting materials.

$$R^1R^2N-A-[\text{thieno[2,3-b]furan with R at position 4}]-SO_2NH_2$$

| A | $R^1$ | $R^2$ | R |
|---|---|---|---|
| 5-$CH_2-$ | $CH_3-$ | $CH_3-$ | H— |
| 4-$CH_2-$ | $CH_3-$ | $CH_3-$ | H— |

-continued

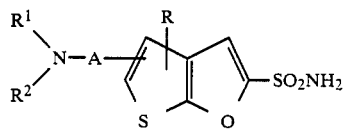

| A | R¹ | R² | R |
|---|----|----|---|
| 5-CH₂— | C₂H₅— | C₆H₅CH₂— | H— |
| 5-CH₂— | H— | C₂H₅— | 4-CH₃— |
| 5-CH₂CH₂— | CH₃— | CH₃— | H— |
| 5-CH₂CH₂— | i-C₄H₉— | H— | 4-CH₃— |
| 4-CH₂— | CH₃— | CH₃OCH₂CH₂— | H— |
| 4-CH₂— | i-C₄H₉— | H— | H |
| 4-CH₂— | —CH₂CH₂—CH₂—CH₂CH₂— | | H |
| 4-CH₂— | —CH₂CH₂—N—CH₂CH₂— <br> $\;\;\;\;\;\;\;\;\;\;\;\;\;\;\;\;\;\;\;$ CH₃ | | H |
| 4-CH₂— | (CH₃)₂NCH₂CH₂— | H | H |

EXAMPLE 2

| 5-(Isobutylaminomethyl)thieno-[2,3-b]furan-2-sulfonamide hydrochloride | 1 mg | 15 mg |
|---|---|---|
| Monobasic sodium phosphate.2H₂O | 9.38 mg | 6.10 mg |
| Dibasic sodium phosphate.12H₂O | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition is adjusted to 5.4–7.4 and diluted to volume. The composition is rendered sterile by ionizing radiation.

EXAMPLE 3

| 5-(Isobutylaminomethyl)thieno-[2,3-b]furan-2-sulfonamide hydrochloride | 5 mg |
|---|---|
| petrolatum q.s. ad. | 1 gram |

The compound and the petrolatum are aseptically combined.

EXAMPLE 4

| 5-(Isobutylaminomethyl)thieno-[2,3-b]furan-2-sulfonamide hydrochloride | 1 mg |
|---|---|
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

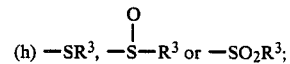

or pharmaceutically acceptable salt thereof wherein

A is $C_{1-8}$ alkylene, either straight or branched chain and either unsubstituted or substituted with $C_{1-3}$ alkoxy or hydroxy; and R is hydrogen or $C_{1-6}$ alkyl either straight or branched chain;

$R^1$ and $R^2$ are independently:
  (1) hydrogen,
  (2) $C_{1-6}$ alkyl, either unsubstituted or substituted with one or more of
    (a) $C_{1-3}$ alkoxy,
    (b) $C_{1-3}$alkoxy-$C_{2-4}$alkoxy,
    (c) hydroxy,
    (d) phenyl, or
    (e) halo,
    (f) pyridyl, pyrimidinyl, pyazinyl or imidazolyl, or
    (g) —NR³R⁴ wherein $R^3$ and $R^4$ are independently selected from
      (i) hydrogen and
      (ii) $C_{1-6}$ alkyl, either unsubstituted or substituted with one or more of $C_{1-3}$ alkoxy, hydroxy or phenyl, or $$(h)\;-SR^3,\;-\overset{O}{\underset{\|}{S}}-R^3\;or\;-SO_2R^3;$$

(3) taken together with the nitrogen atom to which they are attached form a 5 to 7-membered heterocycle.

2. The compound of claim 1 or a pharmaceutically acceptable salt thereof wherein R¹R²N—A— is joined to the 5-position of the thieno[2,3-b]furan ring system.

3. The compound of claim 2, wherein A is —CH₂—.

4. The compound of claim 3, wherein R² is hydrogen and R¹ is $C_{1-6}$ alkyl.

5. The compound of claim 3 which is 5-Isobutylaminomethylthieno[2,3-b]furan-2-sulfonamide or ophthalmologically acceptable salt thereof.

6. The compound of claim 3 which is 5-Methylaminomethylthieno[2,3-b]furan-2-sulfonamide or ophthalmologically acceptable salt thereof.

7. The compound of claim 3 which is 5-(2-Methoxyethylaminomethyl)thieno[2,3-b]furan-2-sulfonamide or ophthalmologically acceptable salt thereof.

8. The compound of claim 3 which is 5-Ethylaminomethylthieno[2,3-b]furan-2-sulfonamide or ophthalmologically acceptable salt thereof.

9. The compound of claim 3 which is 5-(4-Hydroxybutylaminomethyl)thieno[2,3-b]furan-2-sulfonamide or ophthalmologically acceptable salt thereof.

10. The compound of claim 3 which is 5-(2-Pyridylaminomethyl)thieno[2,3-b]furan-2-sulfonamide or ophthalmologically acceptable salt thereof.

11. The compound of claim 3 which is 5-(3-Methoxypropylaminomethyl)thieno[2,3-b]furan-2-sulfonamide or ophthalmologically acceptable salt thereof.

12. The compound of claim 3 which is 5-(2-Ethoxyethylaminomethyl)thieno[2,3-b]furan-2-sulfonamide 5-(Methoxyethoxyethylaminomethyl)thieno[2,3-b]furan-2-sulfonamide 5-(Propylaminomethyl)thieno[2,3-b]furan-2-sulfonamide 5-(Morpholinomethyl)thieno[2,3-b]furan-2-sulfonamide 5-[(Bis-2-Methoxyethyl)aminomethyl]thieno[2,3-b]furan-2-sulfonamide or 5-(2-Fluoroethylaminomethyl)thieno[2,3-b]furan-2-sulfonamide or an ophthalmologically acceptable salt thereof.

13. An ophthalmological formulation for the treatment of ocular hypertension and glaucoma comprising an ophthalmologically acceptable carrier and an effective ocular antihypertensive amount of the compound of claim 1.

14. A method of treating ocular hypertension and glaucoma which comprises the topical ocular administration to a patient in need of such treatment of an effective ocular antihypertensive amount of the compound of claim 1.

* * * * *